US010493186B2

(12) United States Patent
Swain et al.

(10) Patent No.: US 10,493,186 B2
(45) Date of Patent: *Dec. 3, 2019

(54) SYSTEM FOR PROVIDING FLUID FLOW TO NERVE TISSUES

(71) Applicant: KCI Licensing, Inc., San Antonio, TX (US)

(72) Inventors: Larry D. Swain, San Antonio, TX (US); Michael E. Manwaring, San Antonio, TX (US); Braden King-Fung Leung, San Antonio, TX (US); Douglas A. Cornet, Barboursville, VA (US)

(73) Assignee: KCI Licensing, Inc., San Antonio, TX (US)

( * ) Notice: Subject to any disclaimer, the term of this patent is extended or adjusted under 35 U.S.C. 154(b) by 243 days.

This patent is subject to a terminal disclaimer.

(21) Appl. No.: 15/134,161

(22) Filed: Apr. 20, 2016

(65) Prior Publication Data
US 2016/0228623 A1 Aug. 11, 2016

Related U.S. Application Data

(63) Continuation of application No. 12/648,463, filed on Dec. 29, 2009, now Pat. No. 9,351,882.
(Continued)

(51) Int. Cl.
*A61M 1/00* (2006.01)
*A61F 13/00* (2006.01)
*A61B 17/11* (2006.01)

(52) U.S. Cl.
CPC .......... *A61M 1/0088* (2013.01); *A61B 17/11* (2013.01); *A61B 17/1128* (2013.01); *A61F 13/00063* (2013.01); *A61F 13/00068* (2013.01)

(58) Field of Classification Search
CPC .......... A61F 13/00068; A61M 1/0088; A61B 17/11; A61B 17/1128; A61B 2017/1132
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Cell Biology by the Numbers, How Big is a Human Cell?, 2019I, http://book.bionumbers.org/how-big-is-a-human-cell/.*
(Continued)

*Primary Examiner* — Todd J Scherbel

(57) ABSTRACT

An apparatus and system for providing reduced pressure to a defect in a nerve is disclosed. The apparatus comprises a nerve conduit having a generally tubular shape that has walls including a luminal wall surrounding the tissue site to contain fluids within a luminal space between the tissue site to contain fluids within a luminal space between the tissue site and the luminal wall. The apparatus further comprises a manifold having a porous body and a connector for receiving reduced pressure, wherein the manifold is positioned within the luminal space adjacent the tissue site to distribute the reduced pressure to the defect. Additionally, a method for providing reduced pressure to a defect in a nerve is disclosed that includes implanting the nerve conduit and manifold at a site of damaged nerve tissue and applying a reduced pressure to the manifold thereby stimulating repair or regrowth of nerve tissue.

14 Claims, 5 Drawing Sheets

Related U.S. Application Data

(60) Provisional application No. 61/238,770, filed on Sep. 1, 2009, provisional application No. 61/234,692, filed on Aug. 18, 2009, provisional application No. 61/142,053, filed on Dec. 31, 2008, provisional application No. 61/142,065, filed on Dec. 31, 2008.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,833,002 A * | 9/1974 | Palma ................ A61B 17/1128 606/152 |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,778,467 A * | 10/1988 | Stensaas ............ A61B 17/1128 128/898 |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 6,846,294 B2 | 1/2005 | Rastegar et al. |
| 9,351,882 B2 * | 5/2016 | Swain ................ A61B 17/11 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0219471 A1 | 9/2007 | Johnson et al. |
| 2009/0024150 A1 * | 1/2009 | Ahlers ............ A61B 17/1128 606/152 |
| 2009/0326515 A1 * | 12/2009 | Kagan ................ A61F 2/2846 604/543 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |

(56) References Cited

FOREIGN PATENT DOCUMENTS

| | | |
|---|---|---|
| WO | 97/18007 A1 | 5/1997 |
| WO | 99/13793 A1 | 3/1999 |

OTHER PUBLICATIONS

Canadian Examiner Report for corresponding Application No. 2745903, dated Jun. 2, 2017.
Canadian Examiner Report for corresponding Application No. 2745903, dated Sep. 28, 2016.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, The Use of Hypermia in the Postoperative Treatment of Lesions of the Extremities and Thorax, Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

* cited by examiner

SYSTEM FOR PROVIDING FLUID FLOW TO NERVE TISSUES

CROSS-REFERENCED TO RELATED APPLICATIONS

This application is a continuation of U.S. patent application Ser. No. 12/648,463, filed on Dec. 29, 2009, which claims priority to U.S. Provisional Application Nos. 61/142,053 and 61/142,065, each filed on Dec. 31, 2008. This application also claims priority to U.S. Provisional Application No. 61/234,692, filed on Aug. 18, 2009 and U.S. Provisional Application No. 61/238,770, filed on Sep. 1, 2009. Each of the foregoing applications is incorporated herein by reference in their entirety.

BACKGROUND

1. Field of the Invention

The present application relates generally to tissue engineering and in particular to apparatuses and systems suitable for use in treatment of damaged nerve tissue.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formation of granulation tissue. Typically, reduced pressure has been applied to tissue through a porous pad or other manifolding device. The porous pad contains pores that are capable of distributing reduced pressure to the tissue and channeling fluids that are drawn from the tissue. The porous pad often is incorporated into a dressing having other components that facilitate treatment. A scaffold can also be placed into a defect to support tissue growth into the defect. The scaffold is usually bioabsorbable, leaving new tissue in its place.

Scaffolds for reduced pressure treatment are described in, e.g., WO08/091521, WO07/092397, WO07/196590, and WO07/106594. The adequacy of current scaffolds for reduced pressure treatment can be evaluated in light of current knowledge of wound healing. Injury to body tissues results in a wound healing response with sequential stages of healing that include hemostasis (seconds to hours), inflammation (hours to days), repair (days to weeks), and remodeling (weeks to months). A high level of homology exists across most tissue types with regards to the early phases of the wound healing process. However, the stages of healing for various tissues begin to diverge as time passes, with the involvement of different types of growth factors, cytokines, and cells. The later stages of the wound healing response are dependent upon the previous stages, with increasing complexity in the temporal patterning of and interrelationships between each component of the response.

Strategies to facilitate normal repair, regeneration, and restoration of function for damaged tissues have focused on methods to support and augment particular steps within this healing response, especially the latter aspects of it. To this end, growth factors, cytokines, extracellular matrix (ECM) analogs, exogenous cells and various scaffolding technologies have been applied alone or in combination with one another. Although some level of success has been achieved using this approach, several key challenges remain. One main challenge is that the timing and coordinated influence of each cytokine and growth factor within the wound healing response complicate the ability to add individual exogenous factors at the proper time and in the correct coordination pattern. The introduction of exogenous cells also faces additional complications due to their potential immunogenicity as well as difficulties in maintaining cell viability.

Synthetic and biologic scaffolds have been utilized to provide three-dimensional frameworks for augmenting endogenous cell attachment, migration, and colonization. To date nearly all scaffolds have been designed with the idea that they can be made to work with the biology. Traditional scaffolding technologies, however, rely on the passive influx of endogenous proteins, cytokines, growth factors, and cells into the interstitium of the porous scaffold. As such, the colonization of endogenous cells into the scaffold is limited by the distance away from vascular elements, which provide nutrient support within a diffusion limit of the scaffold, regardless of tissue type. In addition, the scaffolds can also elicit an immunogenic or foreign body response that leads to an elongated repair process and formation of a fibrous capsule around the implant. Taken together, these complications can all lead to less than functional tissue regeneration at the injury site.

It would therefore be advantageous to provide additional systems for the repair and remodeling of specialized tissues. The present invention provides such systems.

SUMMARY

The apparatuses, systems and methods of the illustrative embodiments described herein provide active guidance of nerve tissue repair and regeneration through an implanted manifold and nerve conduit. In one embodiment, an apparatus for providing reduced pressure therapy and facilitating growth of nerve tissue in a patient is provided that includes a nerve conduit and nested manifold adaptable for implantation at a damaged nerve site, wherein the manifold provides and distributes reduced pressure at the site of damaged nerve tissue. A manifold according to the invention may also be coupled to a scaffold material which further distributes reduced pressure and provides a structural matrix for growth of the tissue.

In another embodiment, a system for providing reduced pressure therapy and facilitating growth of nerve tissue in a patient is provided that comprises a source of reduced pressure for supplying reduced pressure and a manifold nested in a nerve conduit adaptable for implantation at the tissue site, where the manifold is in fluid communication with the source of reduced pressure. Such a system may also comprise a scaffold material coupled to the manifold which further distributes reduced pressure and provides a structural matrix for the growth of nerve tissue. In a further embodiment, such a system may further comprise a canister for fluid capture and/or a valve for control of reduced pressure in fluid communication with, and positioned between, the manifold and the reduced pressure source. In still a further embodiment, a system according to the invention further comprises a fluid source in fluid communication with the manifold and the damaged nerve tissue.

In a further embodiment, a method of providing reduced pressure therapy and facilitating growth of nerve tissue at a site of nerve tissue damage in a patient is provided that includes implanting a nerve conduit and nested manifold at the tissue site, where the manifold provides a reduced pressure to the damaged nerve tissue. The manifold may also be coupled to a scaffold material, wherein the scaffold material provides a structural matrix for the growth of the nerve tissue. In certain embodiments, the method further comprises providing a manifold in fluid communication with a fluid source, wherein the fluid source may be used to deliver a fluid to the manifold and the damaged nerve tissue. In yet a further embodiment, the fluid source may comprise a fluid comprising one or more bioactive compounds including, but not limited to, an antibiotic, an antiviral, a cytokine, a chemokine, an antibody, and a growth factor.

Other objects, features, and advantages of the illustrative embodiments will become apparent with reference to the drawings and detailed description that follow.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
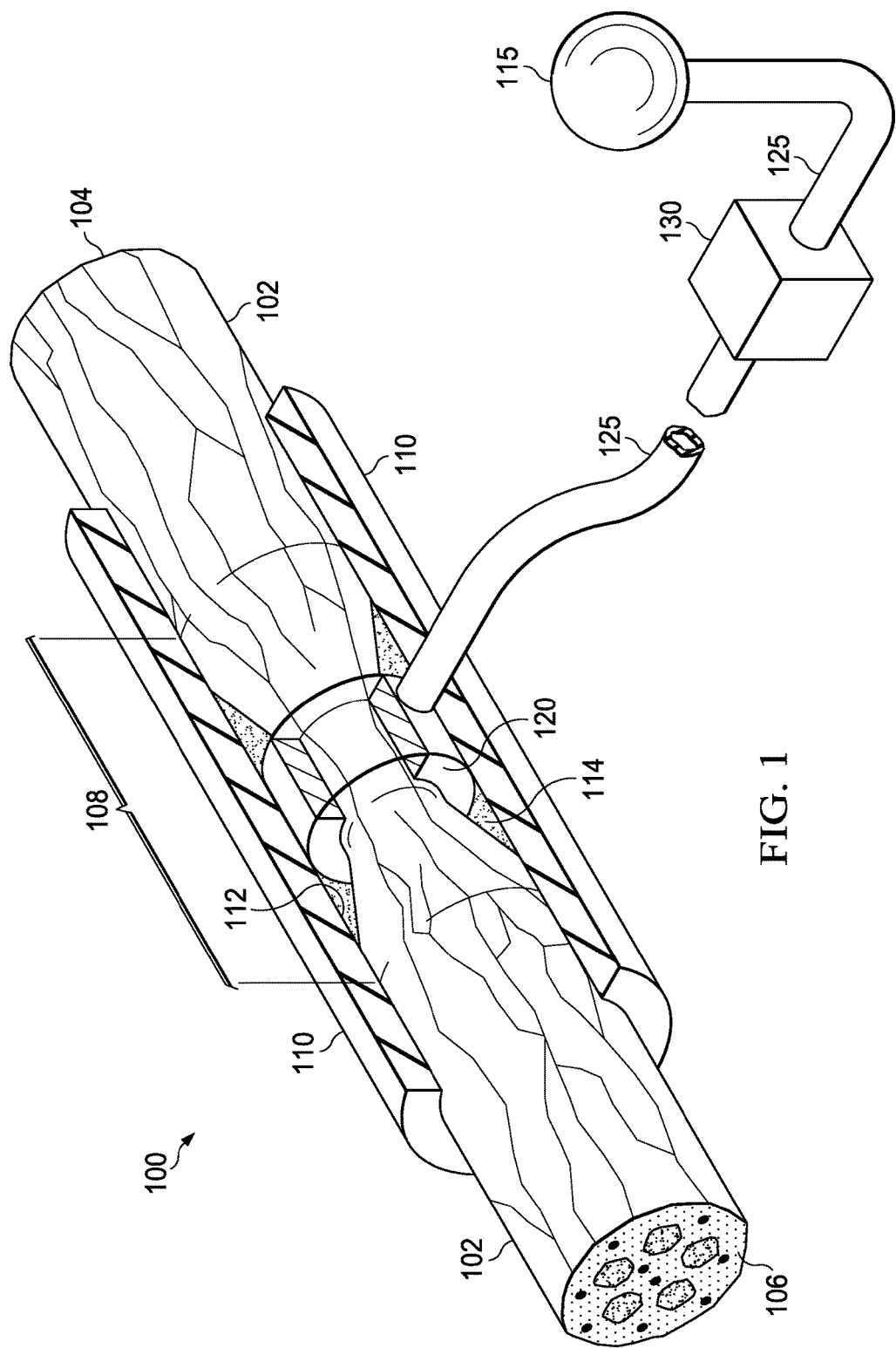
FIG. 1 is a schematic, perspective view of a first reduced-pressure system for repairing a pinched nerve including a nerve conduit and a first embodiment of a manifold with a section of the nerve conduit removed to show the manifold.

Referring to FIG. 1, a reduced pressure therapy system 100 for applying reduced pressure at a tissue site in the body of a patient to repair a defect such as, for example, a damaged nerve is disclosed. The damaged nerve may have been pinched, partially disconnected or severed, or partially degenerated as a result of disease. For example, the damaged nerve in FIG. 1 is a pinched nerve 102 having a proximal segment 104 and a distal segment 106 relative to the central nervous system (CNS) of the patient. The pinched nerve 102 has been damaged at a nerve damage site 108 that has been pinched or partially degenerated, but has not been completely severed. The pinched nerve 102 may be branched or unbranched at the nerve damage site 108. The term "nerve damage site" as used herein refers to a wound or defect located on or within any nerve tissue, including, but not limited to, a disconnected or partially disconnected nerve, a degenerated or partially degenerated nerve, and a compressed or pinched nerve. For example, reduced pressure tissue treatment may be used to enhance repair or regrowth of existing nerve tissue or to facilitate growth or grafted or transplanted nerve tissue and/or cells.

The reduced pressure therapy system 100 comprises a nerve conduit 110 that surrounds the pinched nerve 102 at the nerve damage site 108 with a section of the nerve conduit 110 removed to show the nerve damage site 108. The nerve conduit 110 is substantially tubular in shape and closes the nerve damage site 108 and a portion of the proximal segment 104 and the distal segment 106 that has not been damaged. The nerve conduit 110 has an inner surface 112 that forms a nerve gap 114 with the surface of the nerve damage site 108, i.e., a luminal space between the inner surface 112 of the nerve conduit 110 and the surface of the nerve damage site 108. The reduced pressure therapy system 100 also comprises a reduced pressure source 115 for providing a reduced pressure and a manifold 120 fluidly coupled to the pressure source 115 via a first conduit 125. The manifold 120 is generally tubular in shape and positioned within the nerve gap 114 surrounding the surface of the nerve damage site 108. The manifold 120 may have a variety of shapes depending on the type of nerve damage, and in this particular embodiment has a tubular shape to occupy a portion of the nerve gap 114 around the nerve damage site 108. The manifold 120 may also be coupled to a scaffold material or contain scaffold material (not shown) that provides a structure for tissue growth and repair. The reduced pressure therapy system 100 further comprises a canister 130 fluidly coupled between the reduced pressure source 115 and the manifold 120 via the first conduit 125 to collect bodily fluids such as blood or exudate that are drawn from the nerve gap 114. In one embodiment, the reduced pressure source 115 and the canister 130 are integrated into a single housing structure.

As used herein, the term "coupled" includes direct coupling or indirect coupling via a separate object. The term "coupled" also encompasses two or more components that are continuous with one another by virtue of each of the components formed from the same piece of material. Also, the term "coupled" may include chemical, mechanical, thermal, or electrical coupling. Fluid coupling means that fluid is in communication with designated parts or locations.

In the context of this specification, the term "reduced pressure" generally refers to a pressure that is less than the ambient pressure at a tissue site that is subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be significantly greater than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure. The term "$-\Delta p$" means change in reduced pressure. As used herein, a greater (i.e., more negative) $-\Delta p$ means increased negative pressure (i.e., a greater change in pressure from ambient pressure). Reduced pressure treatment typically applies reduced pressure at −5 mm Hg to −500 mm Hg, more usually −5 to −300 mm Hg, including but not limited to −50, −125 or −175 mm Hg. Reduced pressure may be constant at a particular pressure level or may be varied over time. For example, reduced pressure may be applied and stopped periodically or ramped-up or -down over time.

Figure 2:
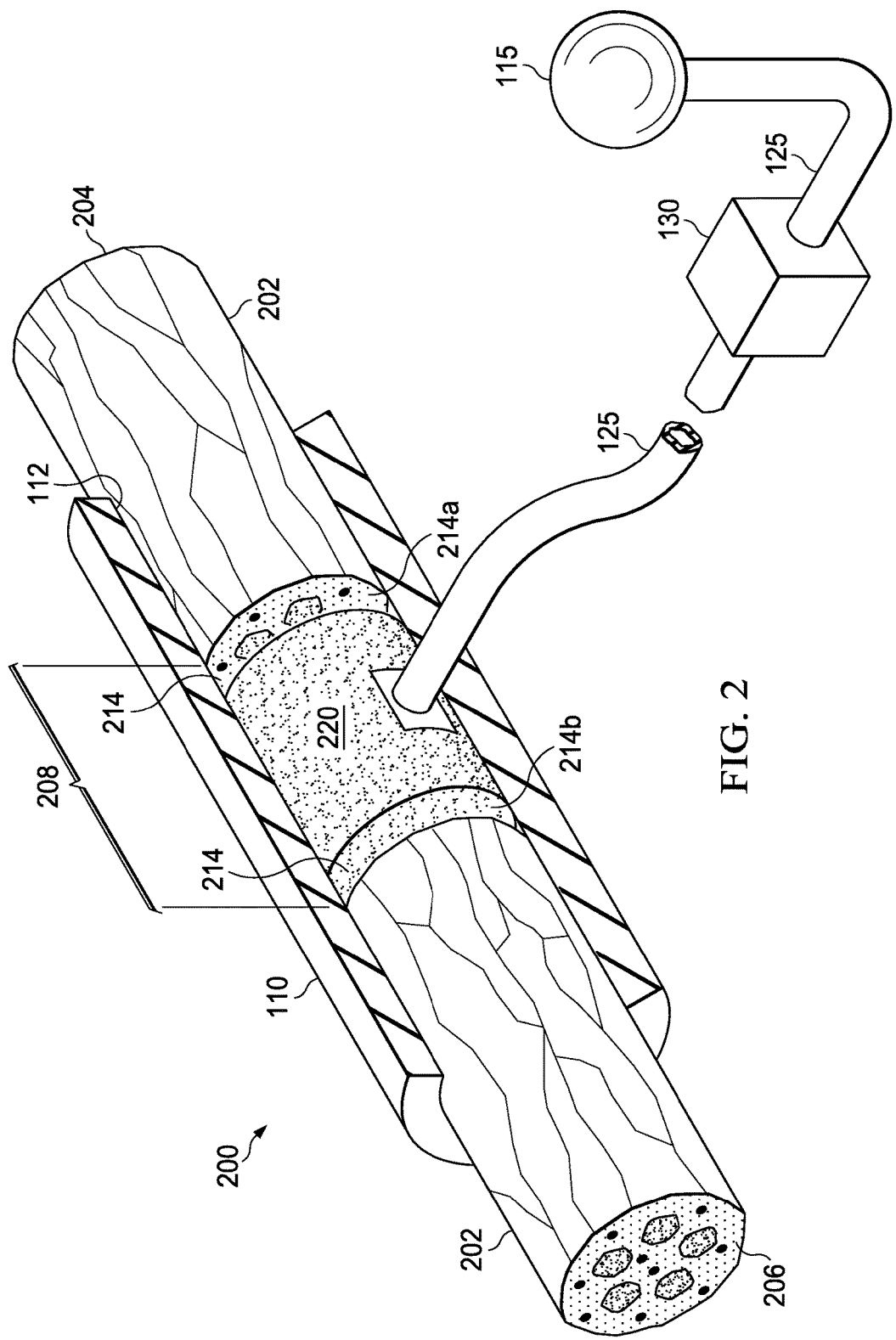
FIG. 2 is a schematic, perspective view of a second reduced-pressure system for repairing a severed nerve including a nerve conduit and a second embodiment of a manifold with a section of the nerve conduit removed to show the manifold.

As indicated above, a nerve damage site may be a wound or defect located on or within any nerve tissue including, for example, a completely severed nerve 202 having a proximal segment 204 and a distal segment 206 relative to the CNS of the patient as shown in FIG. 2. The severed nerve 202 has been damaged at a nerve damage site 208 that has been completely severed. Another reduced pressure therapy system 200 for applying reduced pressure at the nerve damaged site 208 comprises similar components as the reduced pressure therapy system 100. The reduced pressure therapy system 200 comprises the nerve conduit 110 that surrounds the nerve damage site 208 and the severed ends of the severed nerve 202. The inner surface 112 of the nerve conduit 110 forms a nerve gap 214 between the severed ends of the severed nerve 202 within the nerve damage site 208, i.e., a luminal space between the inner surface 112 of the nerve conduit 110 and the surface of the nerve damage site 208. The reduced pressure therapy system 200 also comprises a manifold 220 fluidly coupled to the pressure source 115 via the first conduit 125 and positioned within the nerve gap 214 leaving nerve gaps 214a and 214b between each of the severed ends of the severed nerve 202. The manifold 220 may be generally tubular in shape to enhance fluid flow within the nerve gap 214. The manifold 220 may also be generally cylindrical in shape and function additionally as a scaffold material (not shown) that provides a structure for tissue growth and repair between the severed ends of the severed nerve 202.

Figure 3:
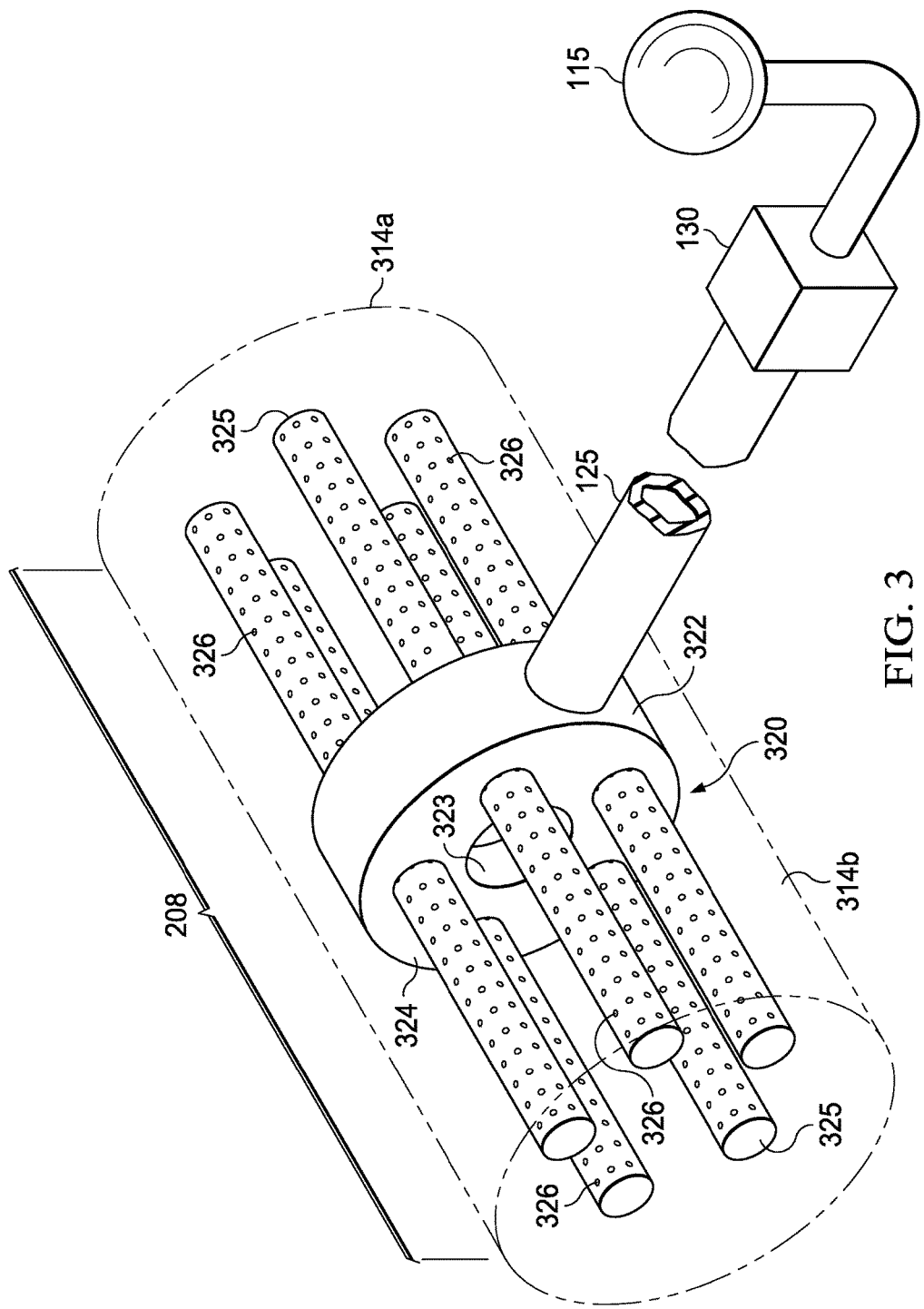
FIG. 3 is a schematic, perspective view of a third embodiment of a manifold for use in the systems shown in FIGS. 1 and 2.

The manifolds 120, 220 shown in FIGS. 1 and 2 create flow patterns and gradients in the nerve gaps 114 and 214 within the nerve damage sites 108 and 208, respectively, which can be further modified to enhance nerve tissue growth. Referring to FIG. 3, a manifold 320 having a core portion 322 with a generally cylindrical shape similar to the other manifolds 120, 220 is shown. The manifold 320 may be used for severed nerve damage, e.g., nerve damage site 208. The core portion 322 of the manifold 320 may also include an axial opening 323 extending between the end surfaces of the core portion 322 (one end surface 324 shown) to accommodate a pinched nerve, e.g., nerve damage site 108. The manifold 320 further comprises manifold rods 325, each one having one end in fluid communication with the end surfaces of the core portion 322 of the manifold 320 and the other end extending axially therefrom within the nerve gaps 314a and 314b at the nerve damage site 208. Any number of manifold rods 325 may be used as required for the re-growth nerve tissue. Furthermore, the manifold 320 may include manifold rods 325 extending from only one of its end surfaces (not shown) so that the core portion 322 may be positioned adjacent the distal or proximal end of the nerve damage site 208. The manifold rods 325 may be generally tubular in shape and formed of the same material as the other manifolds 120, 220 as described above so that they are in fluid communication with the nerve gaps 114 and 214 to promote the formation of new nerve tissue. Hence, the manifold rods 325 may also be bioabsorbable so that there is no need to remove them after new nerve tissue begins forming in the nerve gaps 114 and 214. Alternatively, the manifold rod 325 may comprise a conduit closed at one end and fluidly coupled to the core portion 322 of the manifold 320 at the other end. The walls of this manifold rod 325 may include holes or pores 326 through which the core portion 322 of the manifold 320 fluidly communicates within the nerve gaps 114 and 214.

Figure 4:
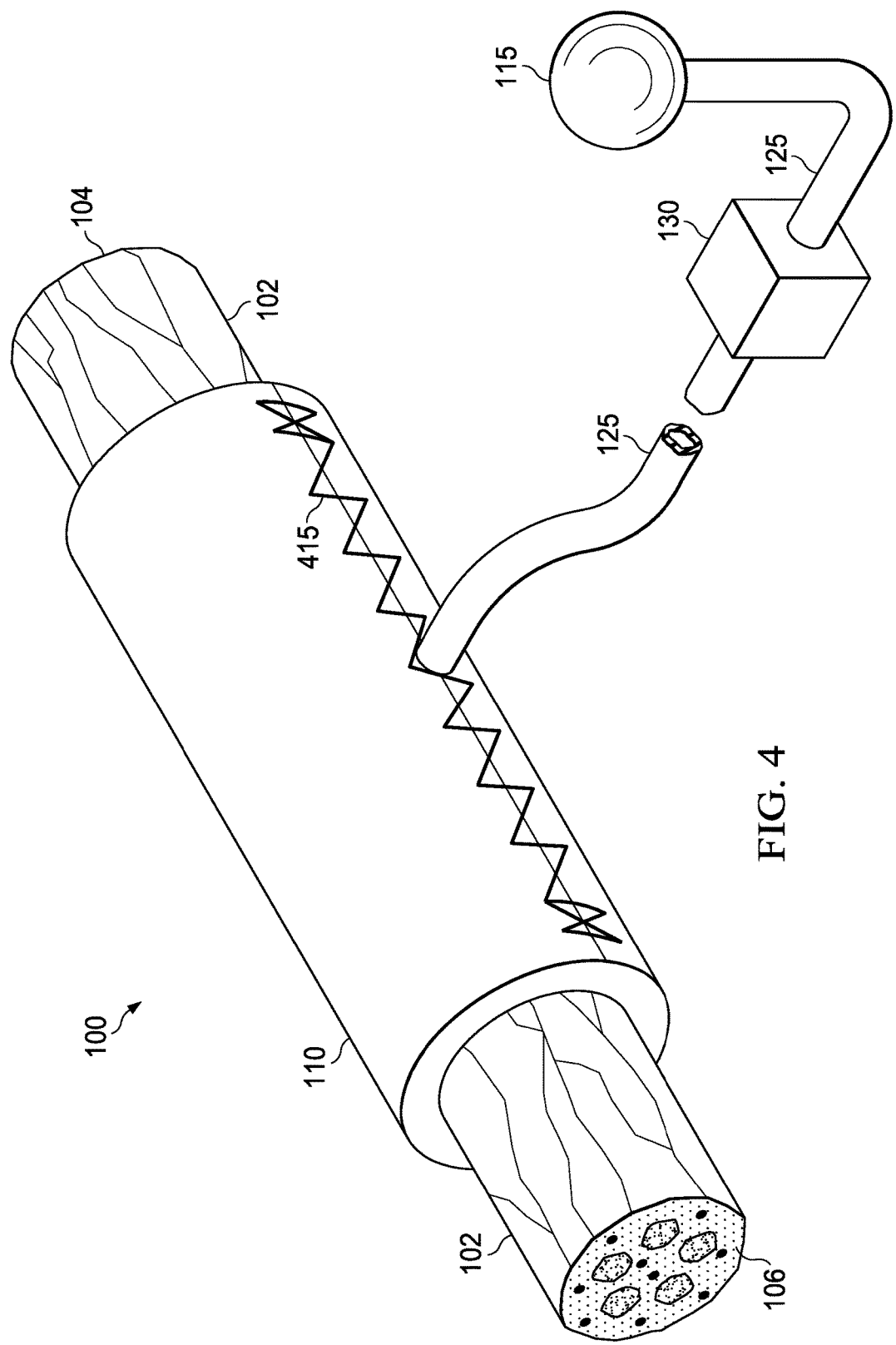
FIG. 4 is a schematic, perspective view of the system shown in FIGS. 1 and 2 showing the nerve conduit enclosing the damaged nerve.

The nerve conduit 110 is shown in FIGS. 1 and 2 with a section removed to show the manifolds 120, 220 and is shown as completely surrounding the nerve damage sites 108, 208 as a closed nerve conduit 310 in FIG. 4. After the manifolds 120, 220 are inserted in the nerve damage sites 108, 208, respectively, the nerve conduit 110 may be sealed by utilizing one or more stitches 415 or any other fastening device known in the art. The nerve conduit 110 may be composed of a bioabsorbable or a bioinert material. Materials that may be used for nerve conduits include, without limitation, polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyorthoesthers, polyethylene glycols, poloxamers, polyphosphazenes, polyanhydrides, polyamino acids, polyacetals, polycyanoacrylates, polyurethanes, polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon. In certain aspects biological (e.g., purified or recombinant) materials may be used form nerve conduits including but are not limited to, fibrin, fibronectin or collagen (e.g., DURAMATRIX™).

A nerve conduit 110 may be an unbroken substantially tubular structure fitted across a gap between a proximal and distal nerve stump such as depicted in FIG. 4. Examples of such substantially tubular nerve conduits, also referred to as nerve guides, include without limitation NEURAGEN® and NEUROFLEX™ collagen conduits. A nerve conduit may also be formed from a wrap that is positioned around a disconnected or damaged (e.g., pinched) nerve and sealed with a closure, such as a suture. Specific examples of wrap-type nerve conduits include, without limitation, NEUROMEND™ and NEURAWRAP™ collagen conduits. In certain aspects, the nerve conduit is made of a material that and encloses the damaged nerve, so as to exclude infiltration of non-nerve cells such as glia. In some embodiments, the nerve conduit material is permeable, thereby allowing fluid and protein factors to diffuse through the conduit. For example, the pores in a nerve conduit may be sufficiently small so as to exclude the entry of cells into the conduit lumen (e.g., pores having an interior diameter or average interior diameter of between about 5 µm and 50 µm, 10 µm and 30 µm or 10 µm and 20 µm). Thus, when reduced pressure is applied to the interior of the conduit fluid and proteins may be drawn to the lumen of the conduit by the pressure gradient. The skilled artisan will recognize that the dimensions of the conduit may be adjusted for any particular nerve application. Generally, the conduits comprise an internal diameter of less than about 6.0 mm, such as about 5, 4, 3, 2.5 or 2 mm.

Figure 5:
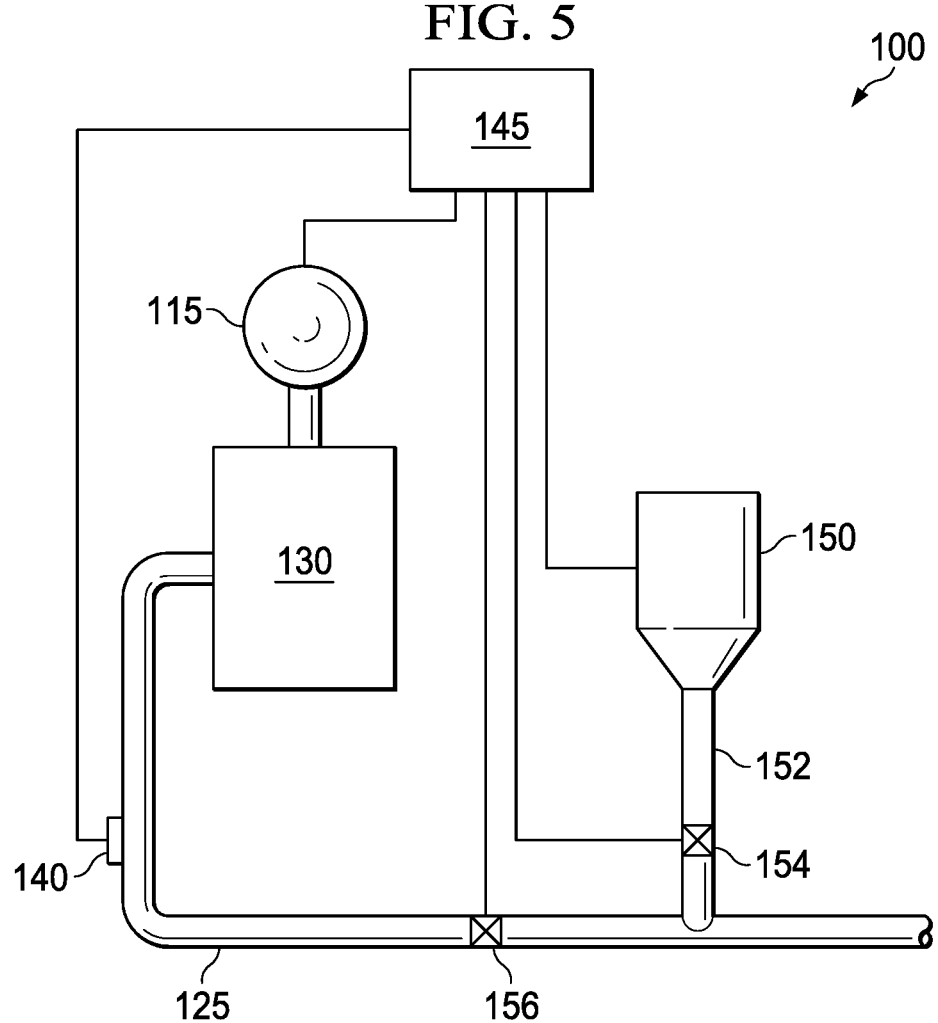
FIG. 5 is a schematic view of a fluid control system for the system shown in FIGS. 1 and 2.

Referring to FIG. 5, the reduced pressure therapy system 100 may further comprise a pressure sensor 140 operably connected to the first conduit 125 to measure the reduced pressure being applied to the manifolds 120, 220. The system 100 further includes a control unit 145 electrically connected to the pressure sensor 140 and the reduced pressure source 115. The pressure sensor 140 measures the reduced pressure within the nerve gap 114, 214 and also may indicate whether the first conduit 125 is occluded with blood or other bodily fluids. The pressure sensor 140 also provides feedback to control unit 145 which regulates the reduced pressure therapy being applied by the reduced pressure source 115 through the first conduit 125 to the manifolds 120, 220. The reduced pressure therapy system 100 may also comprise a fluid supply 150 fluidly coupled to the first conduit 125 via a second conduit 152 and operatively connected to the control unit 145. The fluid supply 150 may be used to deliver growth and/or healing agents to the nerve damage site 108, 208 including, without limitation, an antibacterial agent, an antiviral agent, a cell-growth promotion agent, an irrigation fluid, or other chemically active agents. The system 100 further comprises a first valve 154 positioned in the second conduit 152 to control the flow of fluid therethrough, and a second valve 156 positioned in the first conduit 125 between the reduced pressure source 115 and the juncture between the first conduit 125 and the second conduit 152 to control the flow of reduced pressure. The control unit 145 is operatively connected to the first and second valves 154, 156 to control the delivery of reduced pressure and/or fluid from the fluid supply 150, respectively, to the manifolds 120, 220 as required by the particular therapy being administered to the patient. The fluid supply 150 may deliver the liquids as indicated above, but may also deliver air to the manifolds 120, 220 to promote healing and facilitate drainage at the site of the nerve damage site 108, 208. As used herein, the term "manifold" refers to a substance or structure that is provided to assist in directing reduced pressure to, delivering fluids to, or removing fluids from a tissue site. A manifold can include a plurality of flow channels or pathways that are interconnected to improve distribution of fluids provided to and removed from the area of tissue around the manifold. Examples of manifolds may include, without limitation, devices that have structural elements arranged to form flow channels, cellular foams such as open-cell foam, porous tissue collections, and liquids, gels and foams that include or cure to include flow channels. A detailed description of manifolds and their use according to the invention is provided below.

The term "scaffold" as used herein refers to a substance or structure applied to or in a wound or defect that provides a structural matrix for the growth of cells and/or the formation of tissue. A scaffold is often a three dimensional porous structure. The scaffold can be infused with, coated with, or comprised of cells, growth factors, extracellular matrix components, nutrients, integrins, or other substances to promote cell growth. A scaffold can take on characteristics of a manifold by directing flow through the matrix. A manifold can transmit flow to the scaffold and tissue; in the context of reduced pressure treatment, the manifold can be in fluid communication with the scaffold. A detailed description of scaffolds and their use according to the invention is provided below.

As such, the invention disclosed here discloses methods and apparatuses for controlling cellular-level based patterns of fluid flow that would allow for control of patterned protein organization at a microscopic, nanoscopic, or mesoscopic scale amenable to provide a structured manifold and, optionally, a scaffold material for cellular migration, differentiation, and like behavior necessary for functional regeneration of tissues. In comparison to the passive nature of the current state of the art with regards to tissue repair and regeneration, the methods, scaffolds, manifolds, flow sources and systems disclosed herein provide an active mechanism by which to promote the endogenous deposition of proteins and organization of the provisional matrix with biochemical and physical cues to direct cellular colonization of a scaffold or tissue space. The present invention thus enhances current technology by exploiting the active force of directed fluid flow, providing a framework upon which to design manifolds and scaffolds based upon the need of the biology under the influence of fluid flow. Flow vectors and pathways are utilized to enhance protein deposition and cellular colonization. The systems provided herein are designed to promote establishment of a provisional matrix network with a seamless transition from the healthy tissue edges through a scaffold or tissue site to promote a functional tissue continuum.

Thus, the apparatuses, methods and systems disclosed herein provide a means for active guidance of tissue regeneration through an implanted scaffold or within a tissue site to promote functional recovery. This active guidance occurs through mechanisms of controlled fluid flow, which can be used to initiate or augment the early stages of the body's own natural healing process; a manifold can provide the active guidance necessary to create a controlled fluid flow. Specifically, the controlled flow vectors that the manifolds provide can be used to facilitate the directed influx of cells and proteins into a scaffold. Creation of specific flow pathways within a tissue site or scaffold can lead to patterned deposition of proteins, such as collagen and fibrin within the manifold, scaffold or tissue space. Biochemical cues from cytokines, growth factors, and cells bound within the provisional matrix can work in conjunction with the natural physical cues of the provisional matrix and extracellular matrix to guide the subsequent migration of endogenous cells during the repair stages of healing. These cues act as a form of track that emanates from the healthy tissues and passes through the scaffolding or tissue space to facilitate a continuous guidance pathway for organized tissue regeneration.

To that end, this disclosure provides unique manifolding technologies designed for specific biological needs based upon principles of fluid flow. In certain aspects, the invention concerns a new approach to wound healing, flow (or gradient) activated tissue engineering. In rudimentary form, this approach involves a source or generator of flow that forms a gradient for controlled movement of either endogenous or exogenous fluids into, out of, or through a tissue space for the organized deposition of proteins and/or spatial concentration of cytokines and growth factors, with subsequent formation of a directionally oriented provisional matrix. The tissue space being defined here includes, but is not limited to, the region surrounding a site of nerve tissue damage.

Fluid flow into, through, or out of the nerve tissue space can be refined and directed through the inclusion of additional elements to the system including manifolds and/or scaffolds. The coordinated elements of the system are designed to create flow parameters, pathways, and patterns sufficiently detailed in scale as to be able to influence and direct the controlled adsorption of proteins, the organization of matrix, and organized colonization of specific cell types. Individual elements of the system are as follows.

Source or Generator of Flow.

Flow is induced into, through, or out of the nerve tissue space by methods or apparatuses that introduce changes in mechanical, chemical, and/or electrical potentials. These generators of flow provide either a gradient or a change in potential from the site or reservoir of endogenous or exogenous fluids to the placement position of the flow generator or its extension element (i.e., manifold or scaffold). In one embodiment, the source of flow comprises a source of reduced pressure. Systems and apparatuses according to the invention may also comprise valves or arrays of valves that control the application and amount of negative pressure applied to the manifold. In certain aspects, nerve conduits and/or manifolds described herein comprise a pressure sensor. Thus, in some embodiments, the amount of negative pressure applied by a source is regulated based on the amount of negative pressure that is sensed in the manifold or nerve conduit or at the site of tissue damage.

Manifold.

The flow generators are the driving force for stimulating the flow of fluids. Manifolds are apparatuses for refining the pattern of flow between the source or generator of flow and the tissue space. The macroscale level of flow is refined by specialized manifolds utilized for directed localization to a single point or to a plurality of selectively positioned points for creating initiation sites for microscale flow pathways within the manifold/scaffold and, ultimately, the tissue space. The manifold may also serve as a conduit for the removal of fluids from and as an apparatus for the delivery of exogenous fluids to the tissue space.

A manifold generally refers to a physical substance or structure that serves to assist in applying and translating a mechanical, chemical, electrical or similar alterations into changes in the flow of a fluid, herein defined as the movement of liquids, gases, and other deformable substances such as proteins, cells, and other like moieties. As such, this physical device includes a single point or plurality of points for the egress or evacuation of pressure, fluids, and like substances capable of translating the movement of fluids in a scaffold, as defined above. This can include, but is not limited to, the introduction of exogenous factors such as cells and/or therapeutic moieties into the scaffold through the lumen or plurality of lumens present in the manifold. In addition, as used herein, a manifold includes a single point or plurality of points for the ingress or introduction of fluid from the scaffold back towards the point source of flow.

Flow distributed by the manifold can direct the movement of endogenous proteins, growth factors, cytokines, and cells from their resident locations within the host to the tissue space or scaffold in an organized manner. The establishment of flow along these pathways leads to the deposition of proteins and provisional matrix that creates an interfacial endogenous network connecting the host to the scaffold. Extensions of this matrix can be established within the scaffold through selective positioning of the manifold flow initiation sites with flow promoting scaffolding designs. The organized protein deposition and provisional matrix provide a biochemical and physical framework that stimulates the attachment and migration of cells along directed pathways throughout the scaffold and the tissue space. The resulting endogenous network of proteins, growth factors, and cells provides a foundation upon which subsequent phases of the body's own tissue repair and regeneration mechanisms can build.

When in place, the manifold works in conjunction with a flow generating source and a scaffold, if present. Flow generating sources include, but are not limited to generators of negative pressure; generators of positive pressure; and generators of osmotic flow. The flow gradient established in the manifold may be further refined through the scaffold, to deliver a flow gradient to the scaffold to optimize flow through the scaffold as needed for the particular defect. Many of the embodiments disclosed herein are manifolds capable of translating changes in pressure and the like into controlled movement of fluids, optionally through a physical scaffold, for the purposes of directed tissue regeneration. These embodiments are generally specified for a particular application in the regeneration of specific tissues, but are not limited to a particular tissue therein.

In order to realize the goal of inducing flow for the purpose of tissue regeneration, alterations in the aforementioned mechanical, chemical, or electrical impetus must be translated from the singular gradient source toward a physical substrate or scaffold to elicit cellular-level changes in protein adsorption, matrix organization, cell migration, and other tissue regeneration-related behaviors. These alterations are multivariate in nature and can include mechanical changes that elicit a physical change in pressure applied to the scaffold as applied to the site of the wound or desired site of tissue regeneration, chemical changes that elicit a gradient in protein and/or ion concentrations, which result in the creation of osmotic gradients capable of inducing flow, or electrical changes that create a gradient of current/ion exchange allowing for propagation of electrical signals from the point source. It is to be understood, however, that the applicants are not bound by any particular mechanism through which gradients and fluid flow induce advantageous results in tissue repair or growth. In order to advantageously transmit these gradients to the tissue, a physical device is needed to direct the path of flow from its source to the scaffold or tissue site and vice versa.

In some embodiments, the manifold comprises a physical structure in close apposition to or within the contents of a scaffold and serves to propagate an alteration in a physical parameter, whether it be mechanical, chemical, electrical, or something similar in nature, for the means of directing these changes from its point source to the scaffolding material. The placement of this manifold with respect to its location with regard to that of the scaffold may be of crucial importance for facilitating controlled and directed regeneration of specific tissue types. For example, in peripheral nerve where regeneration primarily occurs in a unidirectional manner from the proximal to distal nerve stumps, it may be important to place the manifold along the length of a nerve conduit more towards it distal end to help direct regeneration towards that end. However, it may also be important to not place the manifold at the most distal aspect of the scaffold/conduit as soluble factors derived from the distal stump have been shown to be important for directing nerve regeneration towards its source.

Manifolds may be composed of a bioabsorbable or bio-inert material. Examples include non-bioabsorbable materials such as medical grade silicone polymers, metals, polyvinylchloride (PVC), and polyurethane. Bioabsorbable polymers such as collagen, polylactic acid (PLA), polyglycolic acid (PGA), polylactide-co-glycolide (PLGA), a polysaccharide, a hydroxyapatite, or a polyethylene glycol, or combinations thereof, can also be used. Some manifolds are also a mix of non-bioresorbable and bioresorbable materials. In general material used for a scaffold may also be used to compose a manifold and such materials are further detailed below. In certain aspects, manifold materials are structured to include a high void fraction for improved bioabsorption properties.

Scaffold.

Biologic and synthetic scaffolds are used in the field of tissue engineering to support protein adhesion and cellular ingrowth for tissue repair and regeneration. The current state of the art in scaffold technology relies upon the inherent characteristics of the surrounding tissue space for the adsorption of proteins and migration of cells. A scaffold for use according to the invention is coupled to a manifold, provides physical guidance to direct the pathway of fluid flow in the tissue site, creating avenues for the movement and migration of adhesive proteins and cells, respectively, which are integral to the establishment of a provisional matrix in predetermined patterns of organization within the tissue space. The methods and apparatuses described for fluid flow-induced and gradient-induced generation of tissues have direct implications into the design of the scaffolds. Within this context, scaffolds serve to refine the pathways of fluid flow within the tissue space to cellular level patterns from the fluid source to the point(s) of flow initiation within the manifold. A scaffold may embody characteristics of a manifold or be combined in conjunction with a manifold for refinement of the flow pathways within the tissue site. In certain aspects, a scaffold is a reticulated structure comprising high void fraction for improved bioabsorption properties.

Nonlimiting examples of suitable scaffold materials include extracellular matrix proteins such as fibrin, collagen or fibronectin, and synthetic or naturally occurring polymers, including bioabsorbable or non-bioabsorbable polymers, such as polylactic acid (PLA), polyglycolic acid (PGA), polylactide-co-glycolide (PLGA), polyvinylpyrrolidone, polycaprolactone, polycarbonates, polyfumarates, caprolactones, polyamides, polysaccharides (including alginates (e.g., calcium alginate) and chitosan), hyaluronic acid, polyhydroxybutyrate, polyhydroxyvalerate, polydioxanone, polyethylene glycols, poloxamers, polyphosphazenes, polyanhydrides, polyamino acids, polyortho esters, polyacetals, polycyanoacrylates, polyurethanes, polyacrylates, ethylene-vinyl acetate polymers and other acyl substituted cellulose acetates and derivatives thereof, polystyrenes, polyvinyl chloride, polyvinyl fluoride, poly(vinylimidazole), chlorosulphonated polyolefins, polyethylene oxide, polyvinyl alcohol, Teflon®, and nylon. The scaffold can also comprise ceramics such as hydroxyapatite, coralline apatite, calcium phosphate, calcium sulfate, calcium carbonate or other carbonates, bioglass, allografts, autografts, xenografts, decellularized tissues, or composites of any of the above. In particular embodiments, the scaffold comprises collagen, polylactic acid (PLA), polyglycolic acid (PGA), polylactide-co-glycolide (PLGA), a polyurethane, a polysaccharide, an hydroxyapatite, or a polytherylene glycol. Additionally, the scaffold can comprise combinations of any two, three or more materials, either in separate areas of the scaffold, or combined noncovalently, or covalently (e.g., copolymers such as a polyethylene oxide-polypropylene glycol block copolymers, or terpolymers), or combinations thereof. Suitable matrix materials are discussed in, for example, Ma and Elisseeff, 2005, and Saltzman, 2004.

Bioactive Agents

In certain aspects, the apparatuses and methods according to the invention concern bioactive agents. Bioactive agents may, in some cases, be incorporated directly onto a manifold or scaffold material (i.e., to generate a bioactive manifold and/or scaffold). For example, agents that facilitate tissue growth such as collagen or fibrin may be directly incorporated onto or into a manifold or scaffold material. Likewise, in applications where aberrant immune response need be avoided (e.g., tissue grafts) immune regulator agents such as rapamycin may be incorporated into manifold or scaffold structures.

In further aspects soluble bioactive agents may be introduced at a site of tissue damage by virtue of the flow through the tissue site. For example, a manifold may be in fluid communication with a fluid source and a bioactive agent may be introduced into the fluid source and thereby into the manifold and damaged nerve tissue.

Nonlimiting examples of useful bioactive growth factors for various applications are growth hormone (GH), a bone morphogenetic protein (BMP), transforming growth factor-α (TGF-α), a TGF-β, a fibroblast growth factor (FGF), granulocyte-colony stimulating factor (G-CSF), granulocyte/macrophage-colony stimulating factor (GM-CSF), epidermal growth factor (EGF), platelet derived growth factor (PDGF), insulin-like growth factor (IGF), vascular endothelial growth factor (VEGF), hepatocyte growth factor/scatter factor (HGF/SF), an interleukin, tumor necrosis factor-α (TNF-α) or nerve growth factor (NGF).

Nerve Tissue Repair and Rngineering.

The apparatuses and systems disclosed herein can be used for nerve tissue repair and engineering in various contexts including the following.

Repair and Regeneration of Lost Tissue.

A generator of flow may be combined with manifolds and/or scaffolds to direct the regeneration of lost tissue at a site of injury or compromised function. Tissues lost from traumatic injury, surgery, burns, or other causes (e.g., infection or autoimmune disease) can be led to regenerate using the methods, scaffolds, manifolds, flow sources and systems of the invention. Functional nerve tissue is directed to regenerate.

Retard the Progression of a Tissue Disease State.

A generator of flow may be combined with manifolds and/or scaffolds to retard disease progression of an affected nerve tissue such as occurs, e.g., in autoimmune disease.

Maintenance of Tissue Viability.

A generator of flow may be combined with manifolds and/or scaffolds to maintain the viability of explanted tissues either for in vitro study, ex vivo scaffold or implant preparation, or in vivo transplant. A generator of flow combined with a manifold may be used to provide nutrient fluid flow to the tissue and to control waste removal from the tissue.

Expansion of Tissue.

A generator of flow may be combined with manifolds and/or scaffolds to promote the expansion of existing tissues. The methods, scaffolds, manifolds, flow sources and systems of the invention can be used to direct the growth of tissues where additional tissue quantity is needed or desired Acceleration of Tissue Formation.

A generator of flow may be combined with manifolds and/or scaffolds to accelerate the rate of tissue formation within a natural healing response. The methods, scaffolds, manifolds, flow sources and systems of the invention may be used to accelerate tissue growth by augmenting formation of provisional matrices, facilitating its stable positioning, and aiding in recruitment of cells to the tissue space.

Stimulating the Differentiation of Stem Cells Along Specific Pathways.

A generator of flow may be combined with manifolds and/or scaffolds to stimulate the differentiation of stem cells or other pluripotent cells into specific lineages. Application of flow using the methods, scaffolds, manifolds, flow sources and systems of the invention may be used to direct pluripotent cells into specific cell lineages needed to foster growth in the tissue space.

Introducing Proteins, Matrix, Cells, or Pharmaceuticals into the In Vivo Environment.

A generator of flow may be combined with manifolds and/or scaffolds to introduce exogenous growth factors, proteins, cells, or pharmaceutical agents into the tissue space to augment tissue repair, regeneration, and/or maintenance.

Creating Matrices In Vitro for Implantation In Vivo.

A generator of flow may be combined with manifolds and/or scaffolds to facilitate formation of matrices in vitro that may subsequently be used for in vivo transplantation.

Promoting Integration of Transplanted Tissue.

A generator of flow may be combined with manifolds and/or scaffolds to promote integration of transplanted tissue into the host environment. This can be applied to autograft, allograft, or xenograft transplants.

Directing Extracellular Matrix (ECM) Deposition and Orientation In Vitro.

A flow generator may be combined with manifolds and/or scaffolds to guide the directed deposition and orientation of ECM expressed by cells and tissues. The directed orientation of ECM has an impact in organizing and directing the attachment and colonization of subsequent cell layers and tissues.

REFERENCES

U.S. Pat. No. 4,787,906
U.S. Pat. No. 6,103,255
U.S. Pat. No. 6,135,116
U.S. Pat. No. 6,365,146
U.S. Pat. No. 6,695,823
U.S. Pat. No. 6,696,575
U.S. Pat. No. 6,767,334
U.S. Pat. No. 6,814,079
U.S. Pat. No. 6,856,821
U.S. Pat. No. 6,936,037
U.S. Pat. No. 6,951,553
U.S. Pat. No. 6,994,702
U.S. Pat. No. 7,004,915
U.S. Pat. No. 7,070,584
U.S. Pat. No. 7,077,832
U.S. Pat. No. 7,108,683
U.S. Pat. No. 7,160,553
U.S. Pat. No. 7,186,244
U.S. Pat. No. 7,214,202
U.S. Pat. No. 7,279,612
U.S. Pat. No. 7,316,672
U.S. Pat. No. 7,346,945
U.S. Pat. No. 7,351,250
U.S. Pat. No. 7,384,786
U.S. Patent Publn. 2003/0225347
U.S. Patent Publn. 2005/0260189
U.S. Patent Publn. 2007/0123895
U.S. Patent Publn. 2008/0033324
U.S. Patent Publn. 2008/0208358
U.S. Provisional Patent Appln. 61/142,053
U.S. Provisional Patent Appln. 61/142,065
Anderson et al., Tissue Eng., 13:2525-38, 2007.
Brody et al., J. Biomed. Mater. Res. B: Appl. Biomater., 83:16-43, 2007.
Gemmiti et al., Tissue Eng., 12:469-79, 2006.
Lago et al., IEEE Trans. Biomed. Eng., 54:1129-37, 2007.
Ma et al., Scaffolding in Tissue Engineering, 2005.
Manwaring et al., Biomaterials, 22:3155-3168, 2001.
Manwaring et al., Biomaterials, 25:3631-3638, 2004.
Mercier et al., Biomaterials, 26:1945-1952, 2005.
Mikos et al., J. Biomed. Mater. Ref., 27:183-189, 2004.
Norman et al., Ann Biomed Eng., 34:89-101, 2006.
PCT Appln. WO 00/38755A2
PCT Appln. WO 00/61206A1
PCT Appln. WO 03/018098A2
PCT Appln. WO 03/092620A2
PCT Appln. WO 04/060148A2
PCT Appln. WO 04/105576A2
PCT Appln. WO 05/009488A2
PCT Appln. WO 05/033273A2
PCT Appln. WO 06/004951
PCT Appln. WO 06/127853
PCT Appln. WO 07/067685A2
PCT Appln. WO 07/092397A2
PCT Appln. WO 07/106589A2
PCT Appln. WO 07/106590A2
PCT Appln. WO 07/106591A2
PCT Appln. WO 07/106592A2
PCT Appln. WO 07/106594A2
PCT Appln. WO 07/133555A2
PCT Appln. WO 07/133556A2
PCT Appln. WO 07/143060A2
PCT Appln. WO 07/196590
PCT Appln. WO 08/013896A2
PCT Appln. WO 08/036162A2
PCT Appln. WO 08/036359A2
PCT Appln. WO 08/036361A2
PCT Appln. WO 08/042481A2
PCT Appln. WO 08/091521A2
Pfister et al., Neurosurgery, 60:137-41, 2007.
Saltzman, Tissue Engineering: Engineering Principles for the Design of Replacement Organs and Tissues, 2004.
Sachlos et al., Cells and Mat., 5:29-40, 2003.
Segvich et al., J. Biomed. Mater. Res. B: Appl. Biomater., 84B:340-349, 2008.
Shimko et al., J Biomed Mater. Res. B: Appl. Biomater., 73:315-24, 2005.
Takahashi et al., Cell, 126:663-76, 2006.
Tan et al., Bone, 41:745-751, 2007.
Tan et al., Biochem. Biophys. Res. Comm., 369:1150-1154, 2008.
Walsh et al., Tissue Eng., 11:1085-1094, 2005.
Wen et al., Handbook of Nanostructured Biomaterials and Their Applications in Nanobiotechnology, 1-23, 2005.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

In view of the above, it will be seen that the advantages of the invention are achieved and other advantages attained. As various changes could be made in the above methods and compositions without departing from the scope of the invention, it is intended that all matter contained in the above description and shown in the accompanying drawings shall be interpreted as illustrative and not in a limiting sense.

We claim:

1. An apparatus for providing reduced pressure to a defect between a first portion of a nerve and a second portion of the nerve, the apparatus comprising:
a manifold formed of a bioabsorbable material and configured to be positioned proximate to the defect, the manifold having a plurality of flow channels configured to distribute reduced pressure to the defect, wherein the manifold comprises a cylindrical shape having an axial opening extending from a first end surface of the manifold to a second end surface of the manifold, the axial opening being parallel to an axis of the manifold;
a plurality of rods coupled to the first end surface of the manifold and extending parallel to the axis of the manifold; and
a wrap having a first end configured to receive the first portion of the nerve and a second end configured to receive the second portion of the nerve and configured to surround the defect and form a luminal space containing the defect and the manifold, the wrap having pores sized to prevent non-nerve cells from entering the luminal space from outside the wrap.

2. The apparatus of claim 1, wherein the manifold has a tubular shape.

3. The apparatus of claim 2, wherein the defect is a pinched nerve between the first portion of the nerve and the second portion of the nerve and the manifold is configured to surround the pinched nerve.

4. The apparatus of claim 1, wherein the defect is a severed nerve having a nerve gap between the first portion of the nerve and the second portion of the nerve, the manifold having a length less than a length of the nerve gap.

5. The apparatus of claim 4, wherein the manifold is configured to be positioned in the nerve gap so that ends of the manifold are separated from an end of the first portion of the nerve and an end of the second portion of the nerve in the absence of reduced pressure.

6. The apparatus of claim 1, wherein the defect is a severed nerve having a nerve gap between the first portion of the nerve and the second portion of the nerve, and the manifold is configured to be positioned in the nerve gap so that the second end surface is adjacent to one of an end of the first portion of the nerve and an end of the second portion of the nerve.

7. The apparatus of claim 1, wherein the plurality of rods comprise wraps having a closed end opposite the first end surface of the manifold.

8. The apparatus of claim 1, wherein the plurality of rods is a first plurality of rods, the apparatus further comprising a second plurality of rods coupled to the second end surface of the manifold and extending parallel to the axis of the manifold.

9. The apparatus of claim 1, wherein the plurality of flow channels are configured to distribute fluid along a directed flow path.

10. The apparatus of claim 1, wherein the manifold is formed from a scaffold material.

11. The apparatus of claim 1, wherein the pores have an interior diameter between about 5 µm and 50 µm.

12. The apparatus of claim 1, further comprising a reduced-pressure source configured to be fluidly coupled to the manifold.

13. The apparatus of claim 1, wherein the manifold is formed of a porous material.

14. The apparatus of claim 1, further comprising a closure configured to seal one end of the wrap to another opposing end of the wrap.

* * * * *